United States Patent [19]

Ghio et al.

[11] Patent Number: 5,512,270
[45] Date of Patent: Apr. 30, 1996

[54] METHOD OF INHIBITING OXIDANTS USING ALKYLARYL POLYETHER ALCOHOL POLYMERS

[75] Inventors: Andrew J. Ghio; Claude A. Piantadosi, both of Durham, N.C.; Thomas P. Kennedy, Richmond, Va.

[73] Assignee: Duke University, Durham, N.C.

[21] Appl. No.: 299,316

[22] Filed: Aug. 31, 1994

Related U.S. Application Data

[63] Continuation of Ser. No. 39,732, Mar. 30, 1993, abandoned.

[51] Int. Cl.$^6$ ................................................. A61K 31/045
[52] U.S. Cl. ..................... 424/45; 424/78.05; 424/78.06; 424/78.08; 424/78.37; 514/887
[58] Field of Search .................................. 424/45, DIG. 1, 424/78.03, 78.05, 78.06, 78.37, 78.08; 514/78, 887, 969, 975

[56] References Cited

U.S. PATENT DOCUMENTS

| | | | |
|---|---|---|---|
| 2,454,541 | 11/1948 | Bock et al. | 525/507 |
| 3,663,230 | 5/1972 | Sato et al. | 430/550 |
| 4,039,669 | 8/1977 | Beyler et al. | 514/178 |
| 4,826,821 | 5/1989 | Clements | 514/78 |
| 4,944,941 | 7/1990 | Ammann | 424/85.5 |
| 5,110,806 | 5/1992 | Clements | 514/78 |
| 5,134,129 | 7/1992 | Lichtenberger | 514/78 |

OTHER PUBLICATIONS

Pimm et al., "Influence of . . . epithelioma", British J–Cancer, vol. 32(1) pp. 62–67 (1975).
Hashimoto et al., "Antimetastatic effect . . . tumors" Tohoku–J–Exp.–Med. 128(3) pp. 259–265 (1979).
McCarty–M F, "An antithrombotic role for . . . pathologies" Med–Hypotheses, 19(4) pp. 345–357 (Apr. 1986).
Wiseman et al., "The Structural mimicry . . . anti–cancer agent" Biochem–Biophys–ACTA, 1138(3) pp. 197–202 (1992).
Wiseman et al., "Droloxifene . . . breast cancer" Cancer–Lett, 66(1) pp. 61–68 (1992).
Kim et al., "Reevaluation of the . . . reduction method" J. Korean Ag. Chem. Society, 36(5) pp. 364–369 (1993).
Kondo et al., "Triton . . . Infection" Japan J. Med. Sci. Biol., 39(2) pp. 35–47 (1986).
Matalon et al., "Mitigation of Pulmonary . . . Surfactant", J. Appl. Physiol., vol. 62, No. 2, pp. 756–761, (Feb. 1987).
Tooley et al., "Lung Function . . . Surfactant," AM. Rev. Respir–Dis., vol. 136, No. 3, pp. 651–656, (Sep. 1987).
Notter, R. H., "Biophysical Behavior . . . Pathophysiology," Semin–Perinatol., vol. 12, No. 3, pp. 180–212 (Jul. 1988).
Baker et al., "Development . . . Enzymes," J.–J.–Appl-–Physiology, vol. 66, No. 4, pp. 1679–1684, (Apr. 1989).
Cornforth et al. Nature,"Antituberculous Effect of Certain Surface–Active Polyoxyethylene Ethers in Mice" vol. 168, pp. 150–153 (1951).
Floyd et al. Journal of Biochemical and Biophysical Methods, "Sensitive Assay of Hydroxyl Free Radical Formation . . ." vol. 10, pp. 221–235 (1984).
Floyd et al. Journal of Free Radicals in Biology & Medicine, "Use of Salicylate With High Pressure Liquid Chromatography . . . ", Vo. 2, pp. 13–18 (1986).

(List continued on next page.)

Primary Examiner—Melvyn I. Marquis
Assistant Examiner—Robert H. Harrison
Attorney, Agent, or Firm—Richard E. Jenkins

[57] ABSTRACT

The present invention relates to use of alkylaryl polyether alcohol polymers as antioxidants to suppress certain oxidant chemical reactions that cause tissue injury and disease in mammals. Disclosed is a method of inhibiting oxidants using alkylaryl polyether alcohol polymers. More particularly, disclosed is a method for the treatment of mammalian disease entities related to overproduction of partially reduced oxygen species comprising administering to a mammal a treatment effective amount of an alkylaryl polyether alcohol polymer. The mammalian disease entities include, but are not limited to, myocardial infarction, stroke, adult respiratory distress syndrome, oxygen toxicity of the lung, lung injury from asbestos, Parkinson's disease, thermal and solar burns of the skin, and injury to the gastrointestinal tract from nonsteroidal anti-inflammatory agents.

8 Claims, 3 Drawing Sheets

OTHER PUBLICATIONS

Glassman, *Science*, "Hemolytic Activity of Some Nonionic Surface–Active Agents", vol. 111, pp. 688–689 (Jun. 23, 1950).

Halliwell et al. *Method In Enzymology*, "Role of Free Radicals . . . ", vol. 186, pp. 1–83 (1990).

Turrens et al., *Journal of Clinical Investigation*, "Protection Against Oxygen Toxicity", vol. 73, pp. 87–95 (Jan., 1984)

Tainter et al. *The New England Journal of Medicine*, "Alevaire as a Mucolytic Agent", vol. 253, pp. 764–767 (1955).

Ghio et al. *American Journal of Physiology, Lung Cellular and Molecular Physiology 7*, "Role of Surface Complexed Iron in Oxidant Generation . . . " vol. 263, pp. L511–L518 (29 Jun. 1992) by Ghio et al.

METHOD OF INHIBITING OXIDANTS USING ALKYLARYL POLYETHER ALCOHOL POLYMERS

This is a continuation of application Ser. No. 08/039,732 filed on Mar. 30, 1993, now abandoned.

BACKGROUND OF THE INVENTION

The present invention relates to use of alkylaryl polyether alcohol polymers as antioxidants to suppress certain oxidant chemical reactions that cause tissue injury and disease in mammals and plants.

Oxygen is life-giving to aerobic plants and animals who depend on it for energy metabolism. It can also be lethal to those same organisms when it is altered from its stable dioxygen ($O_2$) state to any one of three partially reduced species: a) the one electron reduced form superoxide anion ($O_2^-$); b) the two electron reduced form hydrogen peroxide ($H_2O_2$); or the deadly three electron reduced form hydroxyl radical ($^.OH$). In biologic systems $O_2^-$ and $H_2O_2$ are metabolic byproducts of a host of enzymes (oxygenases) that use oxygen as a cofactor. $H_2O_2$ is also produced from $O_2^-$ by the enzymatic action of superoxide dismutases. However, $^.OH$ is generally produced only when $O_2^-$ and $H_2O^2$ interact with transitional ions of metals such as iron and copper in dangerous cyclical redox reactions:

$$O_2^- + Fe^{3+} \rightarrow Fe^{2+} + O_2$$

$$H_2O_2 + Fe^{2+} \rightarrow Fe^{3+} + ^.OH + ^-OH$$

The above reaction is termed the superoxide driven Fenton reaction. The Fenton reaction can also be initiated by other reducing substances such as ascorbate in the presence of ferric ion and $H_2O_2$.

While $O_2^-$ and $H_2O_2$ are each toxic for biologic systems, $^.OH$ (and its alternate hypothesized form the ferryl intermediate $FeO^{2+}$) is a highly reactive species that can oxidize unsaturated membrane lipids, damage cellular proteins and cause mutagenic strand breaks in DNA. To prevent injury from partially reduced $O_2$ species under normal conditions, cells have evolved an elaborate system of antioxidant enzymes (superoxide dismutase, catalase, glutathione peroxidase) and antioxidant molecules (glutathione, alpha-tocopherol, beta carotene). However, when production of partially reduced $O_2$ species exceeds the capacity of cellular antioxidant defenses to contain them, oxidant injury occurs. A growing number of mammalian disease entities are now thought to be related to overproduction of partially reduced $O_2$ species, including the reperfusion injury syndromes, myocardial infarction and stroke, adult respiratory distress syndrome, oxygen toxicity of the lung, lung injury from asbestos, Parkinson's disease, thermal and solar burns of the skin, and injury to the gastrointestinal tract from nonsteroidal anti-inflammatory agents (see Table IV, page 60, Halliwell B and Gutteridge JMC. Methods in Enzymology (1990) 186:1–85). Treatment of these conditions is increasingly directed either toward strategies that prevent enzymatic production of partially reduced $O_2$ species or toward the introduction of exogenous antioxidant compounds that restore oxidant-antioxidant balance in biologic and chemical systems.

Antioxidants are compounds that can be easily oxidized to stable chemical forms. They can protect chemical and biologic systems by sacrificing themselves to oxidation in preference to oxidation of critically important chemical and biologic molecules. Not all oxidizable compounds can perform an antioxidant function. To successfully protect chemical and biologic systems from oxidants, the antioxidant must have a higher reactivity for the oxidant than the chemical or biologic molecule which it seeks to protect. It is theoretically possible to synthesize a multitude of compounds with antioxidant properties. However, the factor limiting use of these antioxidants as treatments in biologic systems is the inherent toxicity of the antioxidant compounds themselves. Thus, it is a major advantage to discover that a class of commonly used and nontoxic ingredients in medicinal pharmacologic preparations are also potent antioxidants. Not only can such compounds react with partially reduced $O_2$ species, but they can be used as treatments for oxidant mediated diseases without themselves causing toxicity to biologic systems.

SUMMARY OF THE INVENTION

As explained below, this invention describes how alkylaryl polyether alcohol polymers are useful as antioxidants in blocking oxidant reactions and biologic injury from partially reduced $O_2$ species. Alkylaryl polyether alcohol polymers are known and used commerically as surface active detergents and wetting agents (U.S. Pat. No. 2,454,541). A structure representative of the class of compounds is where, R=ethylene, $R^1$=tertiary octyl, x is greater than 1, and y=8 to 18. The best known of this class is tyloxapol, a polymer of 4-(1,1,3,3-tetramethylbutyl)phenol with formaldehyde and oxirane. Tyloxapol has been used in human pharmacologic formulations for over 30 years (Tainter ML et al. New England Journal of Medicine (1955) 253:764–767). Tyloxapol is relatively nontoxic and does not hemolyze red blood cells in a thousand times the concentrations at which other detergents are hemolytic (Glassman HN. Science (1950) 111:688-689).

It is the object of the present invention to provide a method to inhibit oxidant chemical reactions caused by partially reduced $O_2$ species.

It is a further object of the present invention to provide a method to protect mammalian tissues against injury from partially reduced $O_2$ species.

It is a further object of the present invention to provide a method for inhibiting oxidant chemical reactions caused by partially reduced $O_2$ species by aerosol treatment with the therapeutic agent.

It is a further object of the present invention to provide a method for inhibiting oxidant chemical reactions caused by partially reduced $O_2$ species by topical application of the therapeutic agent to the skin.

It is an advantage of the present invention that the therapeutic agent is produced from a toxicologically characterized class of compounds with low toxicologic potential to biologic systems.

Consideration of the specification, including the several figures and examples to follow will enable one skilled in the art to determine additional objects and advantages of the invention.

The present invention provides a medicament for the inhibition of injurious effects of partially reduced $O_2$ species in chemical and biologic systems comprising a treatment effective amount of tyloxapol and related alkylaryl polyether alcohol polymers. In preferred embodiments of the invention, the medicament is directly instilled into the respiratory system and administered by aerosolization. In this embodiment, the medicament preferably includes a physiologically acceptable carrier which may be selected from the group consisting of physiologically buffered saline, isotonic saline, and normal saline and an additional treatment effective amount of cetyl alcohol. The pH of the alkylaryl polyether alcohol polymer and carrier mixture is preferably greater than 6.5 but equal to or less than 7.4. In other preferred embodiments of the invention, the medicament is applied topically to the skin. In this embodiment, the medicament preferably includes a physiologic carrier selected from a commercially available petrolatum based ointment or U.S.P. cold cream.

BRIEF DESCRIPTION OF THE DRAWINGS

Reference to the following detailed description may help to better explain the invention in conjunction with the drawings which.

DETAILED DESCRIPTION OF THE INVENTION

Alkylaryl polyether alcohol polymers can in general be synthesized by condensing alkylaryl alcohols with formaldehyde, as described by Bock and Rainey in U.S. Pat. No. 2,454,541 (1948 to Rohm & Haas). Several specific alkylaryl polyether alcohol polymers can be easily synthesized by methods previously described (J.W. Cornforth et al. Nature (1951) 168:150–153). The prototype compound of this class tyloxapol can be conveniently purchased in pharmacologically acceptable purity from Rohm and Haas Co., Philadelphia, Pa.

For treatment of mammalian respiratory conditions related to overproduction of partially reduced $O_2$ species, the alkylaryl polyether alcohol polymer is dissolved in sterile 0.9% NaCl for injection, and the pH is adjusted to approximately 7.0 by addition of NaOH or HCl. A nonpolymeric alkyl or aryl alcohol such as cetyl alcohol (hexadecanol) may be added equivalent to 1–1.5 times the weight of tyloxapol to increase the effectiveness (see FIG. 5 and Table II below) of the mixture in protecting against oxidant injury. This mixture is then administered to the lung by direct instillation into the respiratory system. The mixture may also be administered by aerosolization using a clinically available positive pressure driven nebulizer that produces respirable particles of less than 5 microns mass median diameter. As an example, a 0.125% solution of tyloxapol is made in sterile 0.9% NaCl and double glass distilled deionized water to make it isotonic with respect to respiratory secretions. The pH is adjusted to approximately 7.0 to prevent bronchospasm from extremes of acidity or alkalinity. This mixture is sterilized by vacuum filtration through a 0.22 micron Millipore filter and 3.3 ml each is packaged into 5 ml unit dose glass vials with rubber stoppers fastened with aluminum crimp-on "flip-tear" seals. To provide additional sterilization of product, unit dose vials are terminally autoclaved 12–14 minutes at 125 degrees Centigrade. A 5% concentration of glycerol may be optionally added to the above mixture to stabilize droplet size during aerosolization. For administration of treatment effective doses, 3 ml of sterile tyloxapol solution is inhaled as an aerosol every 4–6 hours using a clinically available positive pressure driven nebulizer (Acorn or deVilbiss). Alternatively, the mixture can be nebulized into the respiratory delivery circuit of a mechanical ventilator. A beta sympathetic agonist bronchodilator (such as 1.25 to 2.5 mg of albuterol) can be mixed with the tyloxapol solution and nebulized concomitantly to prevent any transient bronchospasm that might occur from the tyloxapol solution itself.

For treatment of cutaneous oxidant-mediated disorders such as solar burn, a 0.5 to 5% mixture (w/w) is made with an alkylaryl polyether alcohol such as tyloxapol in a commercially available petrolatum based ointment such as Aquaphor (Beiersdorf, Inc., Norwalk, Conn.), white petrolatum or U.S.P. cold cream as the base vehicle. This mixture is rubbed lightly onto the affected skin area 3 to 4 times daily.

In order to facilitate a further understanding of the invention, the following examples primarily illustrate certain more specific details thereof.

Example I demonstrates the potent activity of alkylaryl polyether alcohol polymers as ˙OH inhibitors in chemical systems. Example II demonstrates the therapeutic benefit of using alkylaryl polyether alcohol polymers to prevent mammalian lung injury from exposure to 100% oxygen.

EXAMPLE I

Inhibition of Oxidants Generated by the Fenton Reaction

Figure 1:
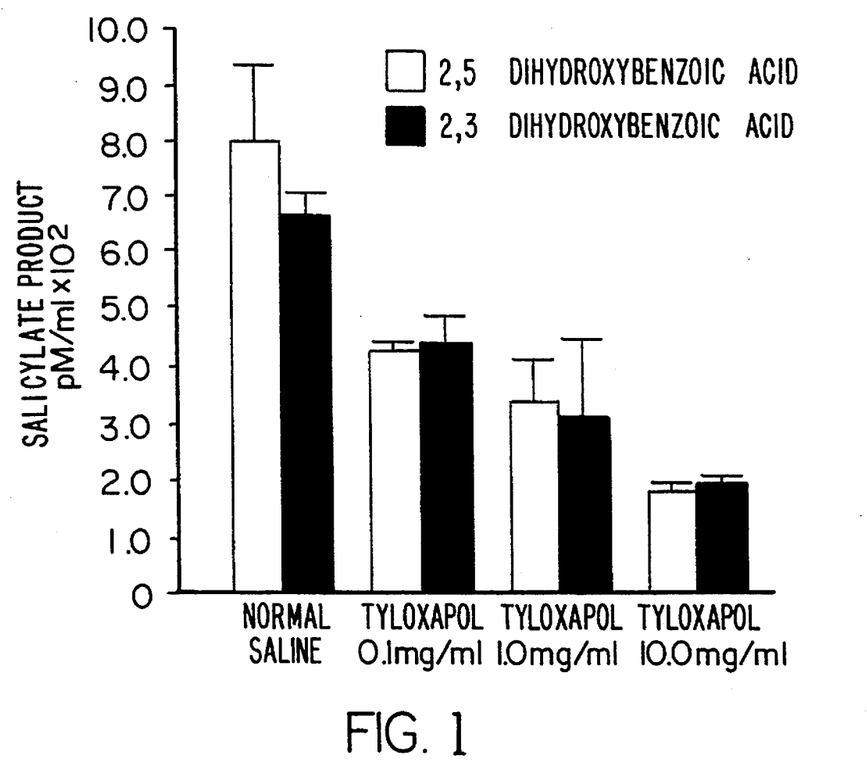
FIG. 1 shows a graph of the inhibitory effect of tyloxapol on ˙OH generation by the Fenton reaction, as measured by hydroxylation of salicylate.

The first chemical system used to test the antioxidant activity of alkylaryl polyether alcohol polymers employed salicylate as the target molecule of oxidants. Hydroxyl radical reacts with salicylic acid (2-hydroxybenzoic acid) to produce two dihydroxybenzoic acid products, 2,3- and 2,5-dihydroxybenzoic acid. These hydroxylated products provide evidence of ˙OH generation (R.A. Floyd et al. *Journal of Biochemical and Biophysical Methods* (1984) 10:221–235; R.A. Floyd et al. *Journal of Free Radicals in Biology & Medicine* (1986) 2:13–18). The detection of 2,3- and 2,5-dihydroxybenzoic acid was performed using high performance liquid chromatography with electrochemical detection. Suspensions of 10 uM $FeCl_3$, 1.0 mM $H_2O_2$, 1.0 mM ascorbate, and 10.0 uM salicylic acid were employed to generate and detect ˙OH. Either 0.1 ml of normal saline or tyloxapol (final concentrations of 0.0 to 10 mg/ml) were added. The reaction mixtures were incubated at 45 degrees Centigrade for 30 min and centrifuged at 1200 g for 10 min. Supernatant was centrifuged (Beckman Microfuge E) through a 0.22 uM microfuge tube filter (PGC Scientific No. 352–118) at 15,000 g. A 100 uL sample of the eluate was injected onto a C18 RP HPLC column (250×4.7 mm, Beckman No. 235329). Hydroxylated products of salicylate were quantified with a Coulochem electrochemical detector (ESA model 5100A) with the detector set at a reducing potential of −0.40 VDC. The guard cell (used as a screen) was set at an oxidizing potential of +0.40 VDC. Measurements were done in duplicate. FIG. 1 shows that the addition of tyloxapol to the reaction mixture inhibited ˙OH generation in a concentration dependent manner.

Figure 2:
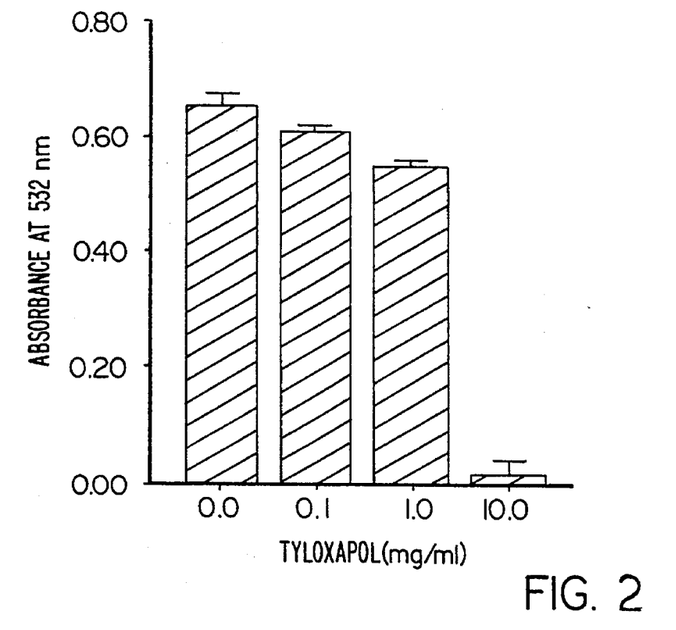
FIG. 2 shows a graph of the inhibitory effect of tyloxapol on ˙OH generation by the Fenton reaction, as measured by oxidation of the sugar 2-deoxyribose.

The second chemical system used to test the antioxidant activity of alkylaryl polyether alcohol polymers employed 2-deoxyribose as the target molecule of oxidants. This pentose sugar reacts with oxidants to yield a mixture of products. On heating with thiobarbituric acid (TBA) at low pH, these products form a pink chromophore that can be measured by its absorbance at 532 nm (B. Halliwell and J.M.C. Gutteridge. Methods in Enzymology (1990) 186:1–85). The chemical system employed to generate oxidants was a reaction mixture containing 10.0 uM $FeCl_3$, 1.0 mM ascorbate, 1.0 mM $H_2O_2$, and 1.0 mM deoxyribose in Hanks Balanced Salt Solution. This system is useful for measuring site-specific ˙OH generation on biologic molecules, as described by Halliwell and Gutteridge in the reference immediately above. Either 0.1 ml of normal saline or tyloxapol (final concentrations of 0.0 to 10.0 mg/ml) were added. The reaction mixtures were incubated at 45 degrees Centigrade for 30 min and centrifuged at 1200 g for 10 min. One ml of both 1.0% (w/v) TBA and 2.8% (w/v) trichloroacetic acid were added to 1.0 ml of supernatant, heated at 100 degrees Centrigrade for 10 min, cooled in ice, and the chromophore determined in triplicate by its absorbance at 532 nm. FIG. 2 shows that the addition of 10 mg/ml tyloxapol to the reaction mixture causes marked inhibition of the oxidation of deoxyribose, as measured by absorbance of the oxidant reaction product at 532 nm.

The third system used to test the antioxidant activity of alkylaryl polyether alcohol polymers employed asbestos as the source of iron for oxidant generation and 2-deoxyribose as the target molecule of oxidants. The generation of oxidants by asbestos has been described previously (A.J. Ghio et al. *American Journal of Physiology* (Lung Cellular and Molecular Physiology 7) (1992) 263:L511–L518). The reaction mixture, in a total volume of 2.0 ml phosphate-buffered saline (PBS), contained the following reagents: 1.0 mM deoxyribose, 1.0 mM $H_2O_2$, 1.0 mM ascorbate, and 1.0 mg/ml crocidolite asbestos. The mixture was incubated at 37 degrees Centigrade for 1 h with agitation and then centrifuged at 1,200 g for 10 min. Oxidant generation was assessed by measuring TBA reactive products of deoxyribose as detailed in the paragraph above. Measurements were done in triplicate. TABLE I below shows that the addition of tyloxapol inhibited in a concentration dependent manner the generation of oxidants by asbestos, as measured by absorbance of the oxidant reaction product at 532 nm.

TABLE I

Effect of Tyloxavol on Oxidant Generation by Asbestos

| | Absorbance at 532 nm |
| --- | --- |
| Tyloxapol 0.0 mg/ml | 0.93 ± 0.02 |
| Tyloxapol 0.1 mg/ml | 0.89 ± 0.04 |
| Tyloxapol 1.0 mg/ml | 0.75 ± 0.01 |
| Tyloxapol 10.0 mg/ml | 0.53 ± 0.04 |

EXAMPLE II

Protection from Mammalian Lung Injury by 100% Oxygen

To determine if alkylaryl polyether alcohol polymers could protect against oxidant injury to intact biologic systems, this treatment was studied in a well established model of oxygen toxicity to the lung (J.F. Turrens et al. *Journal of Clinical Investigation* (1984) 73:87–95). Sixty-day old male Sprague-Dawley rats (Charles River, Inc., Wilmington, Mass.) were tracheally instilled with 0.5 ml of either normal saline, tyloxapol (6.0 mg) or tyloxapol (6.0 mg) and cetyl alcohol (hexadecanol, 11.0 mg). These rats (n=10 in each treatment group) were then exposed to either air or 100% oxygen in plexiglass chambers at a flow rate of 10 liters/min. Oxygen percentage was monitored by a polarographic electrode and maintained continuously above 98%. Temperature was maintained between 20 and 22 degrees Centigrade. Survival times were determined by checking animals every 4 hours. Separate groups of rats treated similarly (n=10 in each treatment group) were exposed to 100% oxygen for 61 hours, and then were euthanized with 100 mg/kg intraperitoneal pentobarbital. Pleural fluid volume was measured by aspirating pleural fluid from the chest cavity through a small incision in the diaphragm. Lung wet/dry weight ratios were calculated from the left lung after drying the tissue for 96 hours at 60 degrees Centigrade. Survival data in shown in TABLE II below. Rats receiving intratracheal tyloxapol had markedly improved survival compared to placebo control animals instilled with saline. The protective effect of tyloxapol was further enhanced by combining it with cetyl alcohol.

TABLE II

Effect of Tyloxapol on Oxygen Toxicity in Rats
Percent Survival

| Hours | Saline | Tyloxapol | Tyloxapol/Cetyl Alcohol |
| --- | --- | --- | --- |
| 0 | 100 | 100 | 100 |
| 58 | 100 | 100 | 100 |
| 62 | 83 | 100 | 100 |
| 66 | 42 | 100 | 100 |
| 70 | 17 | 75 | 100 |
| 72 | 17 | 75 | 100 |
| 76 | 8 | 58 | 100 |
| 80 | 8 | 58 | 100 |
| 84 | 8 | 58 | 100 |
| 88 | 8 | 58 | 100 |
| 92 | 0 | 58 | 100 |
| 96 | 0 | 58 | 100 |

Figure 3:
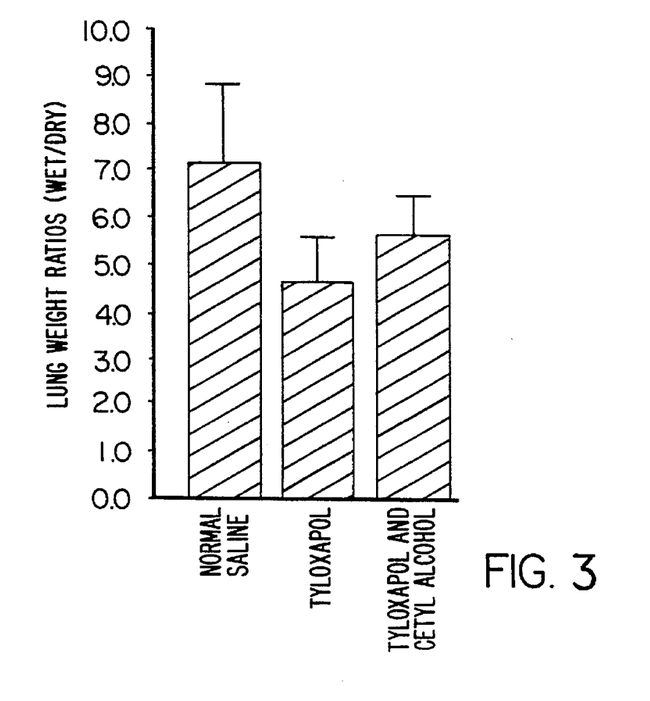
FIG. 3 shows lung wet/dry weight ratios in rats exposed to 100% oxygen and treated with normal saline, tyloxapol, and tyloxapol plus cetyl alcohol.
Figure 4:
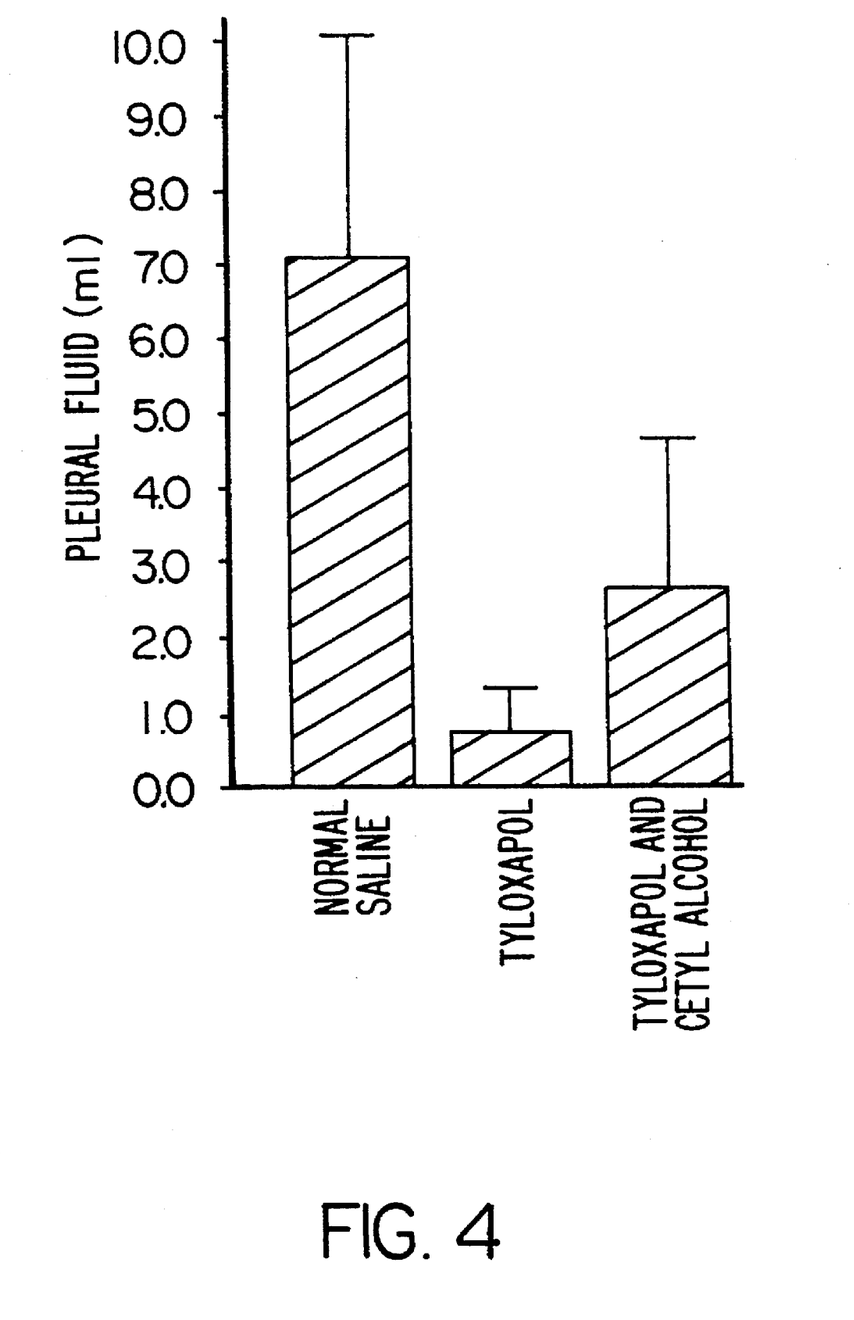
FIG. 4 shows pleural fluid in rats exposed to 100% oxygen and treated with normal saline, tyloxapol, and tyloxapol plus cetyl alcohol.

Lung wet/dry weight ratios were substantially lower in rats treated with tyloxapol or tyloxapol and cetyl alcohol (FIG. 3), demonstrating that tyloxapol or the combination of tyloxapol and cetyl alcohol protect against edema formation from oxidant injury. Rats treated with tyloxapol or the combination of tyloxapol and cetyl alcohol also had less pleural fluid accumulation than saline treated controls (FIG. 4). These results demonstrate the ability of alkyaryl polyether alcohol polymers such as tyloxapol to protect against oxidant tissue injury. The survival studies (TABLE II) further demonstrate that the protective effect of the medicament is enhanced by combining it with alcohols such as cetyl alcohol.

The appended claims set forth various novel and useful features of the invention.

What is claimed is:

1. A method for the treatment of mammalian disease entities resultant from oxidant species consisting essentially of administering to a mammal an amount of alkylaryl polyether alcohol polymer of the formula $$\left[ \underset{R^1}{\underset{|}{\bigcirc}}^{O(RO)yH} - CH_2 - \underset{R^1}{\underset{|}{\bigcirc}}^{O(RO)yH} \right]_x$$

where, R=ethylene, $R^1$=tertiary octyl, x is greater than 1, and y=8 to 18, effective to inhibit oxidant chemical reactions caused by the oxidant species in the mammal, thereby treating the mammalian disease entities.

2. The method of claim 1, wherein said carrier is selected from physiologically buffered solutions.

3. The method of claim 2, wherein the physiologically buffered solutions are selected from the group consisting of isotonic saline, normal saline, and combinations thereof.

4. The method of claim 1, wherein the mammalian disease entities are selected from the group consisting of myocardial infarction, stroke, adult respiratory distress syndrome oxygen toxicity of the lung, lung injury from asbestos Parkinson's disease, thermal and solar burns of the skin, injury to the gastrointestinal tract from nonsteroidal anti-inflammatory agents, and combinations thereof.

5. The method of claim 1, wherein said administering of said alkylaryl polyether alcohol polymer is directly into the mammal's respiratory tract.

6. The method of claim 1, wherein said administering of said alkylaryl polyether alcohol polymer is by aerosolization.

7. The method of claim 1, wherein said administering of said alkylaryl polyether alcohol polymer is by application to the mammal's skin.

8. The method of claim 1, wherein said administering of said alkylaryl polyether alcohol polymer includes a physiologically acceptable carrier.

\* \* \* \* \*

UNITED STATES PATENT AND TRADEMARK OFFICE
CERTIFICATE OF CORRECTION

PATENT NO. : 5,512,270
DATED : April 30, 1996
INVENTOR(S) : Andrew J. Ghio, et al.

It is certified that error appears in the above-indentified patent and that said Letters Patent is hereby corrected as shown below:

On the Cover page, Column 2, Publication References, last line, delete "Vo." and insert --Vol.-- therefor.

Column 3, line 59, delete "FIG. 5 and".

Column 4, line 19, delete "concommitantly" and insert --concomitantly-- therefor.

Column 5, line 14, after "Gutteridge" delete the period (.) and insert a comma (,) therefor.

Column 5, line 53, in the sub-heading in Table I, delete "Tyloxavol" and insert --Tyloxapol-- therefor.

Column 6, line 21, delete "in" (first occurrence) and insert --is-- therefore.

Column 7, last line, after "syndrome" insert a comma (,).

Column 8, line 1, after "asbestos" insert a comma (,).

Signed and Sealed this

Seventeenth Day of December, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,512,270
DATED : April 30, 1996
INVENTOR(S) : Ghio et al.

It is certified that error appears in the above-identified patent and that said Letters Patent is hereby corrected as shown below:

Column 2, lines 25-35 and column 7, lines 1-10, before the formula, each occurrence, insert --[-- such that the formulas appear as:

In the Claims:

Column 7, claim 2, line 1, "claim 1" should read --claim 8--.

Signed and Sealed this

Twenty-eighth Day of September, 1999

Attest:

Q. TODD DICKINSON

*Attesting Officer*   *Acting Commissioner of Patents and Trademarks*